United States Patent [19]
Workman et al.

[11] Patent Number: 5,240,225
[45] Date of Patent: Aug. 31, 1993

[54] PLASTIC SLUMP CONE

[75] Inventors: Gary Workman, Lombard; John M. Fitzgerald, Lake Bluff, both of Ill.

[73] Assignee: Deslauriers, Inc., Bellwood, Ill.

[21] Appl. No.: 775,413

[22] Filed: Oct. 15, 1991

[51] Int. Cl.⁵ .................... B28B 7/00; G01N 11/00
[52] U.S. Cl. .................... 249/117; 73/54.03; 73/864.59; 249/139; 249/DIG. 4
[58] Field of Search .............. 249/117, 139, 160, 164, 249/DIG. 4; 73/54.03, 864.53, 864.59

[56] References Cited

U.S. PATENT DOCUMENTS

| | | | |
|---|---|---|---|
| 3,163,908 | 1/1965 | Lawmaster | 249/164 |
| 3,527,439 | 9/1970 | Lawmaster | 249/DIG. 4 |
| 4,047,690 | 9/1977 | Winter et al. | 249/DIG. 4 |
| 4,842,241 | 6/1989 | Fitzgerald et al. | 249/DIG. 4 |

Primary Examiner—Jay H. Woo
Assistant Examiner—James P. Mackey
Attorney, Agent, or Firm—Wood, Phillips, VanSanten, Hoffman & Ertel

[57] ABSTRACT

A plastic slump cone includes a unitary frusto-conical mold formed of a synthetic resin defining an open base at one axial end and a smaller open top at an opposite axial end for receiving a sample of freshly mixed concrete, in use. A pair of foot pieces formed of synthetic resin are secured to the mold and extend radially outwardly therefrom at the base on opposite sides thereof for holding the mold firmly in place while filling with a sample of concrete. A pair of handles formed of synthetic resin are secured to the mold and extend radially outwardly therefrom intermediate the base and the top and opposite sides thereof for lifting the mold when filled with a sample of concrete.

7 Claims, 2 Drawing Sheets

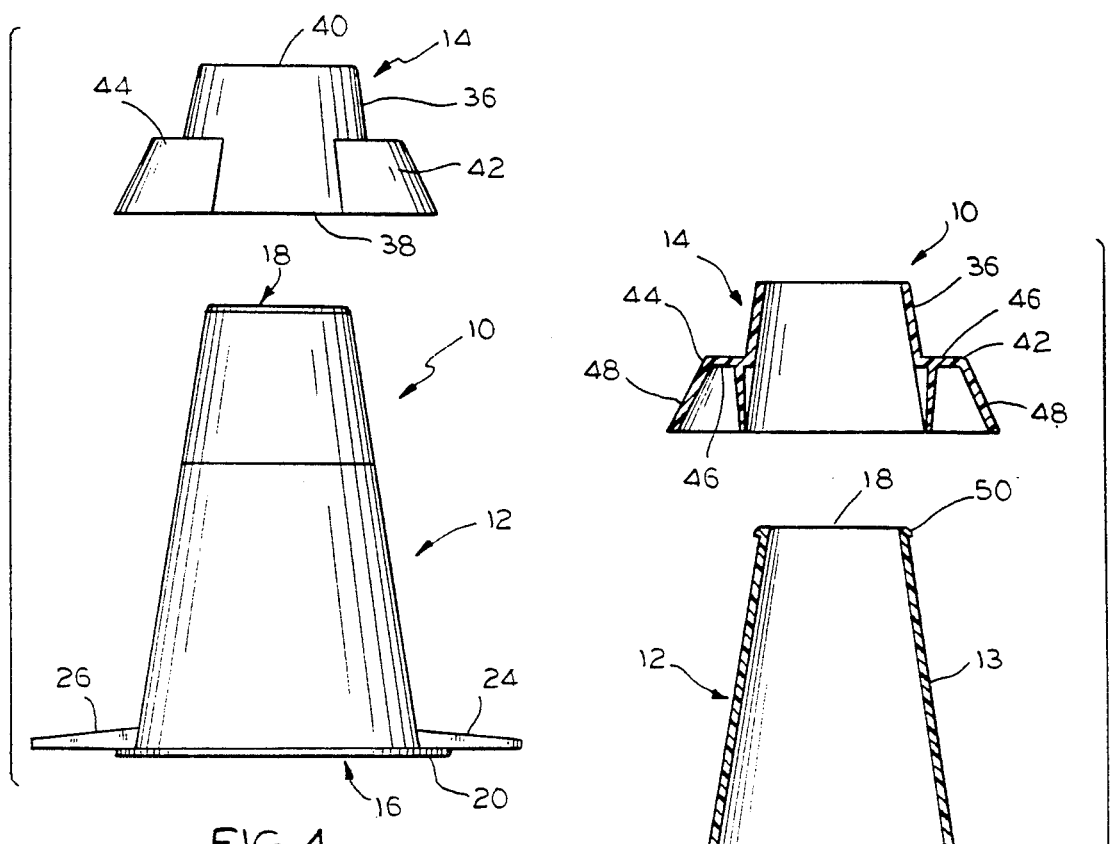
FIG. 4
FIG. 5
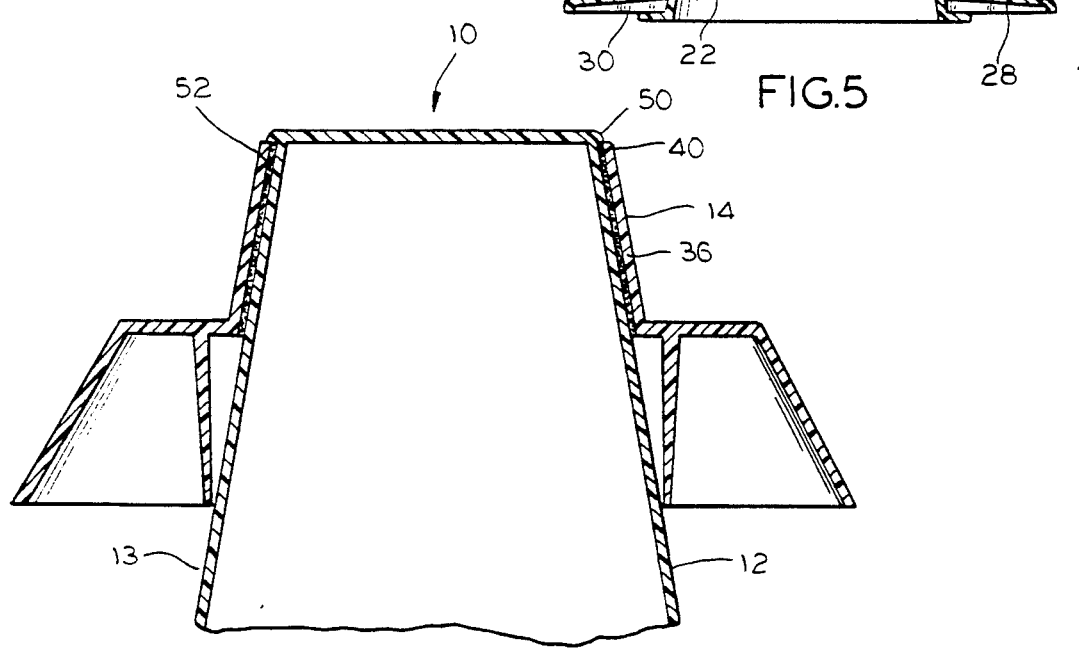
FIG. 6

PLASTIC SLUMP CONE

FIELD OF THE INVENTION

This invention relates to a slump cone used for determining slump of concrete and, more particularly, to a slump cone formed of synthetic resin.

BACKGROUND OF THE INVENTION

In construction projects it is often necessary that the concrete used satisfy certain specifications. In order to ensure that the concrete satisfies the specifications it is necessary to take certain tests. One such test is known as a slump test. A slump test is performed by pouring and compacting a sample of freshly mixed concrete in a frusto-conically shaped mold. After the concrete is compacted the mold is lifted allowing the concrete to subside. The displacement of the center of the top surface defines the slump of the concrete.

Currently, the standard test for the slump of concrete is performed using a mold made of metal. The mold is frusto-conically shaped and includes bottom foot pieces which a user can stand on or which fasten into clamps on a base plate while filling the mold with a sample of concrete Once the mold is filled and the sample compacted, a pair of handles on opposite sides of the mold are used to lift the mold. Typically, the foot pieces and handles are also formed of metal and are welded to the molds. Further, the mold is often formed of a flat piece of metal turned to form a cone with opposite edges being secured as by riveting. Such a construction results in a seam in the interior surface of the mold. Another method is having the mold made with a metal spinning process which results in a seamless steel mold.

The above-described metal mold gives rise to numerous problems. For example, the molds are generally somewhat heavy and owing to the materials used in the required manufacturing steps can be relatively expensive The weight renders them more difficult to handle. Also, the mold can be easily dented during handling at a construction site rendering the mold useless The concrete often adheres to the metal walls of the mold and the moisture in the concrete can cause rusting of the same. As specifications require the mold to be relatively smooth and free from projections, concrete sticking on the walls as well as the rivets coming loose might also render the mold non-usable.

The present invention is directed to overcoming one or more of the problems discussed above in a novel and simple manner.

SUMMARY OF THE INVENTION

In accordance with the invention, there is disclosed a slump cone formed of plastic.

Broadly, there is disclosed herein a plastic slump cone comprising a unitary frusto-conical mold formed of a synthetic resin defining an open base at one axial end and a smaller open top at an opposite axial end for receiving a sample of freshly mixed concrete, in use. A pair of foot pieces formed of synthetic resin are secured to the mold and extend radially outwardly therefrom at the base on opposite sides thereof for holding the mold firmly in place while filling with a sample of concrete. A pair of handles formed of synthetic resin are secured to the mold and extend radially outwardly therefrom intermediate the base and the top and opposite sides thereof for lifting the mold when filled with a sample of concrete It is a feature of the invention that the foot pieces are integrally formed with the mold.

It is another feature of the invention to provide a unitary frusto-conical holder formed of a synthetic resin defining an open base at one axial end and a smaller open top at an opposite axial end, the holder top having a diameter slightly greater than that of the mold top and the holder being of a height less than that of the mold to be telescopically received and secured thereon, and wherein the handles are integrally formed with the holder.

It is a feature of the invention that the mold top includes a radially outwardly extending flange having an outer diameter slightly greater than an inner diameter of the holder top to retain the holder on the mold.

It is another feature of the invention that a body of adhesive is disposed between the holder and the mold for securing the holder on the mold.

Further features and advantages of the invention will readily be apparent from the specification and from the drawings.

BRIEF DESCRIPTION OF THE DRAWINGS

FIG. 4 is an exploded elevation view similar to that of FIG. 2 showing a holder separated from a mold;

FIG. 5 is a sectional view similar to that of FIG. 4; and

FIG. 6 is a partial view illustrating securing of the holder to the mold.

DETAILED DESCRIPTION OF THE DRAWING

Figure 1:
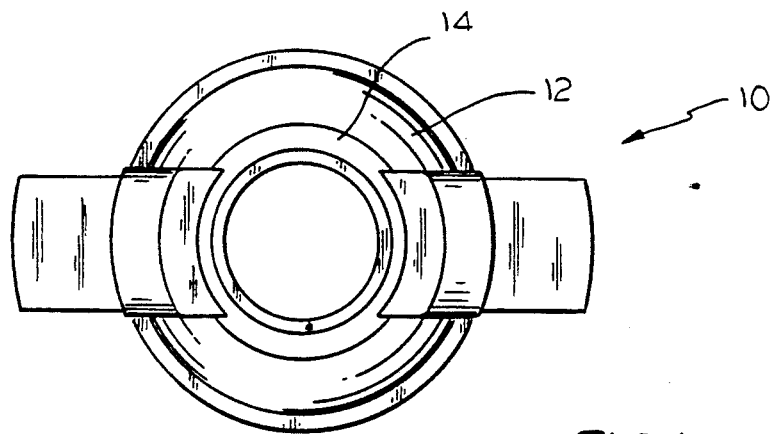
FIG. 1 is a top plan view of a plastic slump cone according to the invention.
Figure 2:
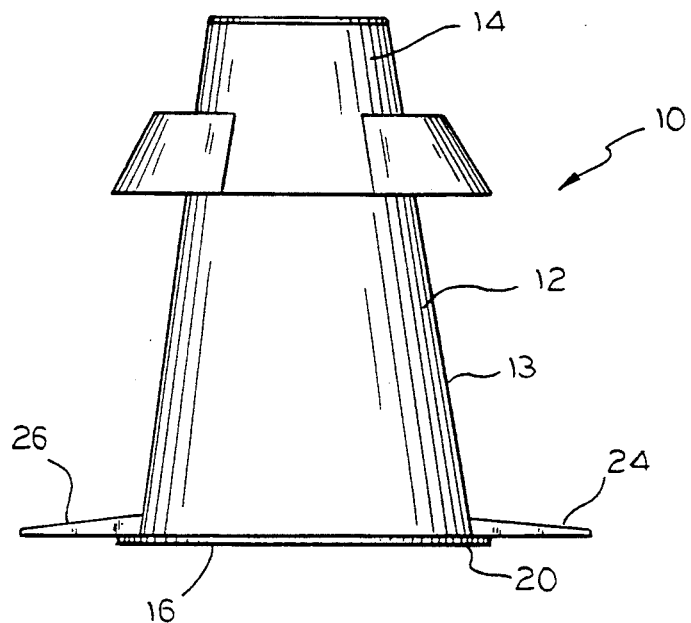
FIG. 2 is a side elevation view of the slump cone of FIG. 1.

With reference to the drawing, a plastic slump cone 10 used for performing concrete slump tests is illustrated. The slump cone 10 is of two piece construction and includes a mold 12 and a holder 14.

Figure 3:
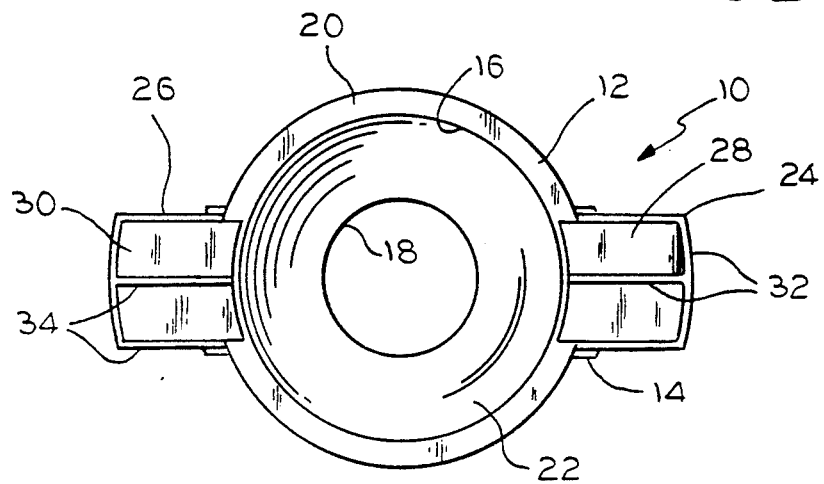
FIG. 3 is a bottom plan view of the slump cone of FIG. 1.

The mold 12 comprises a unitary element formed of synthetic resin. The mold 12 includes a frusto-conical sidewall 13 defining an open base 16 at one axial end and a smaller open top 18 at an opposite axial end. A radially outwardly extending flange 20 extends around the periphery at the base 18. In the illustrated embodiment of the invention, the mold 12 is four inches in diameter at the top 18 and eight inches in diameter at the base 16. The height between the base 16 and top 18 is twelve inches. The mold 12 being molded of synthetic resin includes no seams on an inner surface 22, as particularly illustrated in FIG. 3.

Secured to the mold 12 as by being integrally formed therewith are a pair of foot pieces 24 and 26. The foot pieces 24 and 26 comprise radially outwardly extending members adapted to be stepped on by the feet of a user thereof or which fasten into clamps on a base plate. The underside 28 and 30 of the foot pieces 24 and 26, respectively, include suitable respective ribs 32 and 34 to add stiffening and strength thereto. The flange 20 is continuous about the periphery of the base 16 except in the area proximate the foot pieces 24 and 26 to accommodate requirements for forming the mold 12 which is typically done as by injection molding the same.

Because of their requirements for molding the slump cone 10, the holder 14 is formed separate and apart from the molds 12. The holder 14 comprises a unitary frusto-conical sidewall 36 also formed of a synthetic resin. The wall 36 defines an open base 38 at one axial end and a smaller open top 40 at an opposite axial end. The holder top 40 has an inner diameter slightly greater than an outer diameter of the mold top 18. The holder 14 is of a height less than that of the mold 12 to be telescopically received thereon, as illustrated in FIGS. 1-3 and 6. The holder 14 includes a pair of integral handles 42 and 44 extending radially outwardly therefrom intermediate the base 38 and top 40 on opposite sides. Each handle 42 and 44 comprises a top wall 46 connected to a downwardly extending peripheral wall 48.

The slope of the holder wall 36 is identical to that of the mold wall 13 to be effectively telescopically received thereon. A dual form of securement is provided for retaining the holder 14 to the mold 12. Particularly, the mold 12 at the top end 18 includes a radially outwardly extending flange 50 having an outer diameter slightly greater than an inner diameter of the holder top 40. When the holder 14 is placed on top of the mold 12, a relative deformation results between the mold top flange 50 and the holder wall 36 at the top 40 until the holder 14 is lowered to the fullest extent possible. At such time, the flange 50 provides a snap fit securement as by extending outwardly over the top 40, as is particularly illustrated in FIG. 6. Additionally, prior to placing the holder 14 on the mold 12, a body 52 of adhesive is placed either at the top of the mold 12 or on the inside of the holder sidewall 36. The body of adhesive 52 upon setting provides a further securement between the holder 14 and the mold 12. Alternatively, the holder 14 and the mold 12 can be welded, such as with vibrational or ultrasonic welding.

For manufacturing purposes, the mold 12 and holder 14 are molded separately. These parts can then be assembled at the manufacturing site or assembled at a construction site To perform the standard test for the slump of concrete the user stands on the foot pieces 24 and 26 while filling the mold 12 with a sample of concrete Once the mold 12 is filled and the sample compacted, the handles 42 and 44 are used to lift the holder 14 and the mold 12 secured thereto.

Owing to the use of the described plastic construction, the cone 10 is relatively lightweight and easier to handle and can be manufactured for considerably lower costs. Further, the use of plastic for forming the cone 10 provides easier cleaning and eliminates the possibility of rusting. Also, the concrete does not stick to the plastic as it might to a metal device. Moreover, owing to the deformable aspects of synthetic resin made products, the cone 10 will not permanently dent. While it may be temporarily dented due to mishandling at a construction site, the deformability of the synthetic resin made components will result in them returning to their original shape.

The embodiment of the invention disclosed herein is illustrative of the broad inventive concepts comprehended hereby.

We claim:

1. A plastic slump cone comprising:
   a unitary seamless frusto-conical cone section formed of a synthetic resin defining an open base at one axial end and an open top at an opposite axial end for receiving a sample of freshly mixed concrete, in use, said open top of said cone section being smaller than said open base of said cone section;
   a pair of foot pieces formed of synthetic resin and secured to said cone section and extending radially outwardly therefrom at the base on opposite sides thereof for holding the cone section firmly in place while filling its with a sample of concrete;
   a pair of handles formed of synthetic resin and secured to said cone section and extending radially outwardly therefrom intermediate said base and said on opposite sides thereof for lifting said cone section when filled with a sample of concrete, and
   a unitary frusto-conical holder formed of a synthetic resin defining an open base at one axial end and an open top and an opposite axial end smaller than said open base of said holder, the holder top having a diameter slightly greater than that of the cone section top and the holder being of a height less than that of the cone section to be telescopically received and secured thereon, and wherein said handles are integrally formed with said holder.

2. The plastic slump cone of claim 1 wherein said cone section top includes a radially outwardly extending flange having an outer diameter slightly greater than an inner diameter of the holder top to retain said holder on said cone section.

3. The plastic slump cone of claim 1 further comprising a body of adhesive disposed between said holder and said cone section for securing said holder on said cone section.

4. The plastic slump cone of claim 1 further comprising means for securing said holder to said cone section.

5. A two piece plastic slump cone comprising:
   a unitary, seamless frusto-conical cone section formed of a synthetic resin defining an open base at one axial end and an open top at an opposite axial end for receiving a sample of freshly mixed concrete, in use, said open top of said cone section being smaller than said open base of said cone section and including a pair of integral foot pieces extending radially outwardly therefrom at the base on opposite sides thereof for holding the cone section firmly in place while filling it with a sample of concrete;
   a unitary frusto-conical holder formed of a synthetic resin defining an open base at one axial end and an open top at an opposite axial end smaller than said open base of said holder, the holder top having a diameter slightly greater than that of the cone section top and the holder being of a height less than that of the cone section to be telescopically received thereon, and a pair of integral handles extending radially outwardly therefrom intermediate said base and said top on opposite sides thereof for lifting said cone section when filled with a sample of concrete; and
   means for securing said holder on said cone section.

6. The two piece plastic slump cone of claim 5 wherein said securing means comprises said cone section top including a radially outwardly extending flange having an outer diameter slightly greater than an inner diameter of the holder top to retain said holder on said cone section.

7. The two piece plastic slump cone of claim 5 wherein said securing means comprises a body of adhesive disposed between said holder and said cone section for securing said holder on said cone section.

* * * * *